United States Patent [19]
Krzyminski

[11] Patent Number: 5,373,364
[45] Date of Patent: Dec. 13, 1994

[54] HAND-HELD INSTRUMENT FOR MEASURING REFLECTIONS ON COLORED CONTROL FIELDS OF PRINTED SHEETS

[76] Inventor: Harald Krzyminski, Wiesbadener Strasse 27, D-61462 Königstein, Germany

[21] Appl. No.: 199,562

[22] Filed: Feb. 22, 1994

[30] Foreign Application Priority Data

Feb. 26, 1993 [DE] Germany .................. 4305968

[51] Int. Cl.$^5$ .................................. G01J 3/51
[52] U.S. Cl. ........................ 356/405; 356/406; 356/419
[58] Field of Search ............ 356/402, 405, 406, 407, 356/416, 418, 419, 425, 446; 250/226

[56] References Cited

U.S. PATENT DOCUMENTS

| | | | |
|---|---|---|---|
| 3,995,958 | 12/1976 | Pfahl et al. | 356/425 |
| 4,003,660 | 1/1977 | Christie, Jr. et al. | 356/425 |
| 4,264,210 | 4/1981 | Mitsuhashi | 356/432 |
| 5,141,323 | 8/1992 | Kipphan et al. | 356/419 |

Primary Examiner—F. L. Evans
Attorney, Agent, or Firm—Collard & Roe

[57] ABSTRACT

To enable top illumination densitometers to be used for measuring light reflections on colored control fields of so-called printing control strips, it is necessary to center the measuring openings of such instruments accurately on the control field so as to focus properly. For this purpose, there is provided a hand-held instrument which comprises an instrument housing and a measuring head in the housing, the measuring head having an outer wall, defining a measuring aperture facing the measuring plane and containing a source of measuring light and a measuring light receiver arranged to receive light from the source through light guiding channels. The light guiding channels include a tubular light guiding channel portion extending perpendicularly to the measuring plane along the outer wall from the measuring aperture up the measuring head, and the tubular light guiding channel portion having a uniform cross section along the entire height of the measuring head, the cross section not exceeding that of a control field to be measured.

11 Claims, 2 Drawing Sheets

HAND-HELD INSTRUMENT FOR MEASURING REFLECTIONS ON COLORED CONTROL FIELDS OF PRINTED SHEETS

BACKGROUND OF THE INVENTION

1. Field of the Invention

The present invention relates to a hand-held instrument for measuring reflections on a colored control field of a printed sheet.

2. Description of the Prior Art

Instruments of this type are used in the printing industry in the form of color measuring instruments and top color illumination densitometers for controlling the color flow in printing machines, particularly in multi-color screen printing. Usually, the measurements are not taken within the printed image but on so-called printing control strips which are printed along the margins of the printed sheets. These printing control strips are normally arranged along the entire width of the printed sheet so as to permit the control of the color flow for each printed location. To enable the requirement of the colored printing inks in the various zones of the printing machine to be determined, measurements must be made for metering the color flow or measuring the color density, for which purpose various instruments have been used. The printing control strips are sub-divided into a succession of small control fields for the individual color zones. The control fields may be printed integrally over the entire surface or in dots, or two or more colors may be printed over each other for controlling their co-action. It is desirable to keep the control fields as small as possible because, in the first place, the marginal control strips reduce the size of the useful printed sheet and, secondly, it is desired to place several control fields within the color zone width of 30 to 40 mm to obtain the necessary measurement values for each of the four to five printing ink colors used. Most printing control strips have control fields of a size not exceeding 6×6 mm, and the size of the usually round measuring apertures of densitometers is between 3 mm and 3.5 mm. The limited size of the control fields poses a special problem for commercially available hand-held measuring instruments because the aperture of the measuring head must be focussed as accurately as possible over the center of the control field and the measuring heads are substantially larger than the control fields. This makes it impossible visually to control the positioning of the measuring aperture when the measuring head is placed on the control field.

The size of the measuring head is determined by various factors. First, a number of structural parts must be built into the measuring head, such as a source of the measuring light, a receiver of the measuring light, including usually several photo elements with filters, and light guiding channels, including optical components, for guiding the light from the source and the reflected light from the control field to the receiver. Various standards furthermore require particular arrangements for the structural parts. For example, top color illumination densitometers may be standardized for a 45°/0° measuring geometry or a 0°/45° measuring geometry, which means that the illuminating measuring light is selectively guided and the reflected light is collected at 45° and 0° relative to the measuring plane. This measuring geometry in conjunction with the similarly standardized small aperture angles of +/−5° for the illuminating and reflected light means that the size of the measuring head is about 30 mm in diameter and 30 mm to 50 mm in height, and the measuring aperture is normally located on or near the center axis of the measuring head. This applies to measuring heads of round, quadratic or rectangular cross section. To make it possible to center such measuring heads with their measuring apertures accurately over the center of the control fields, known densitometers of this type have finders. The finder is affixed to the bottom plate of the instrument and is comprised of a thin plate defining a usually round hole of the same size as the measuring aperture of the measuring head. The measuring instrument proper is hinged or otherwise connected to the bottom plate so that it may be lowered. Thus, the finder may be visibly controllably positioned over the center of the control field to be measured, while the instrument is raised. The measuring head may then be lowered, which in more recent instruments has not been done manually but with a motor-driven measuring head.

These known instruments have substantially three disadvantages. They are technically complex and expensive in the first place and, secondly, they are not user friendly because they require a very careful positioning of the finder and the measuring instrument. The most serious disadvantage is the fact that the user cannot view the selected control field during the measurement because it is covered by the measuring head. It is, therefore, impossible to notice displacements of the measuring instrument relative to the control field, which may readily occur during the lowering of the instrument. This may result in false measuring results when the control field is measured not at its center but at a margin or if it is even partially or completely out of range.

Another type of hand-held measuring instruments has a rigidly mounted measuring head. The accurate positioning of such an instrument with respect to a spot to be measured is achieved by strongly tapering the measuring head downwardly. U.S. Pat. No. 4,264,210 discloses a dot measuring instrument with an arm carrying a light receiver unit in the form of a vertical cylinder. Accurate positioning of this instrument can be obtained only if the measuring plane is viewed under an oblique angle. If the user looks down more or less vertically on the measuring instrument and the measuring plane, accurate positioning is impossible because the carrying arm and the upwardly widening shape blocks the view from above. It must be noted in this respect that all such known instruments have light receiving units which widen towards the top, particularly instruments which are designed not only to test films with transmitted light but also copies with top illumination. The instruments must have two light guiding channels for measuring copies with top illuminations, one channel portion for guiding the measuring light illuminating the spot to be measured and another channel portion for guiding the reflected light.

Instruments with such rigid measuring heads cannot be used for measuring printed sheets, and particularly the control fields of printing control strips, because it is preferred to look down vertically when visually judging the printing quality. This more or less vertical orientation of viewing the printed sheet has the purpose to exclude the disturbing influence of surface gloss and reflections from the visual judgment of the colors. For this purpose, testing tables for printed sheets or printing control strips have obliquely positioned table tops on which the printed sheets are placed. This enables a person standing in front of the table to look more or less perpendicularly down on the table. Therefore, the densitometers used for this purpose comprise the above-described combination of movable measuring head and finder. The instruments with a fixed measuring head are used almost exclusively for simple black-and-white densitometers. The measurements are made at selected spots on the film or the black-and-white picture so that the difficulty of centering the measuring aperture geometrically accurately over a limited control field under the aggravated conditions of color measurement do not exist.

SUMMARY OF THE INVENTION

It is the primary object of this invention to provide a hand-held measuring instrument of the first-indicated type with a simple structure enabling a vertical sighting of the control field without obstruction by the instrument and an accurate centering of the measuring aperture on the control field.

The above and other objects are accomplished according to the invention with a hand-held instrument for measuring reflections on a colored control field of a printed sheet extending in a measuring plane, which comprises an instrument housing and a measuring head in the housing, the measuring head having an outer wall arranged to face a user of the instrument and the measuring head defining a measuring aperture facing the measuring plane. The measuring head contains a source of illuminating light, a light receiver, and light guiding channels arranged to guide the illuminating light from the source through the measuring aperture to a respective one of the control fields in the measuring plane and light reflected therefrom through the measuring aperture to the light receiver. The light guiding channels include a tubular light guiding channel portion rising perpendicularly to the measuring plane along the outer wall from the measuring aperture up the measuring head, and the tubular light guiding channel portion has a uniform cross section throughout the length thereof, the cross section not exceeding that of a control field to be measured.

The measuring aperture is immediately adjacent the outer wall of the measuring head, which faces the user of the instrument, at the lower end of the vertically rising tubular light guiding channel portion which is a part of the measuring head. It is essential that the outer cross section of this channel portion is not larger than the area of the control field, preferably even a little smaller, and that this cross section is uniform throughout the height of the measuring head, rather than upwardly widening, and that no carrying arm blocks the view of the control field from above. This vertical light guiding channel portion is accommodated in a small elongated boss projecting from the outer wall of the measuring head and this boss constitutes the sighting element which enables the measuring aperture to be accurately centered over each control field of a printing control strip. In addition to avoiding all the above-enumerated disadvantages of known measuring instruments, the light measuring instrument of the present invention is much simpler than that disclosed in U.S. Pat. No. 4,269,210, and since the tubular light guiding channel portion is integrated in the measuring head, it cannot be damaged from the outside and requires no special protective devices.

BRIEF DESCRIPTION OF THE DRAWING

The above and other features, objects and advantages of this invention will become more apparent from the following detailed description of now preferred embodiments, taken in conjunction with the accompanying, somewhat schematic drawing wherein.

DETAILED DESCRIPTION OF THE PREFERRED EMBODIMENTS

Figure 1:
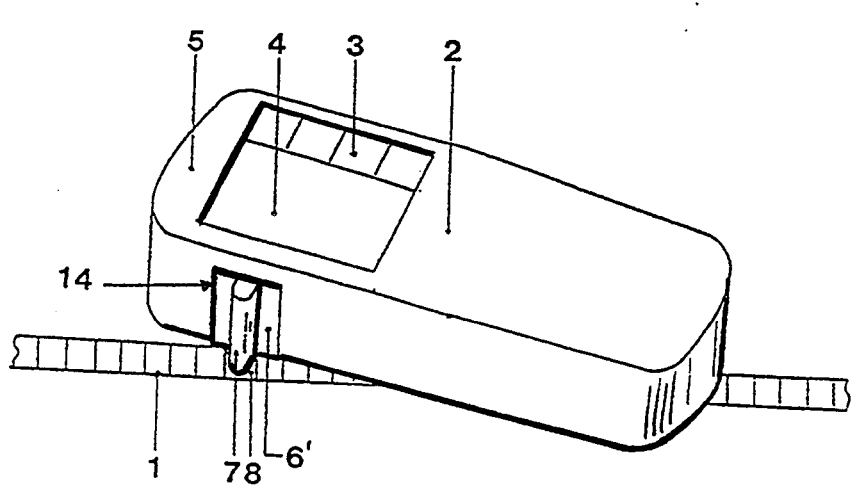
FIG. 1 is a perspective view showing the hand-held instrument placed on a printing control strip for measuring one of its control fields.

Referring now to the drawing and first to FIG. 1, there is shown a hand-held instrument 2, i.e. a top illumination densitometer, for measuring reflections on a colored control field 8 of a printed sheet 1 extending in a measuring plane, i.e. a conventional printing control strip which has a succession of control fields. As is well known, such an instrument comprises operating elements 3, i.e. a row of buttons, and a display 4 showing the functions and measured values.

Figure 4B:
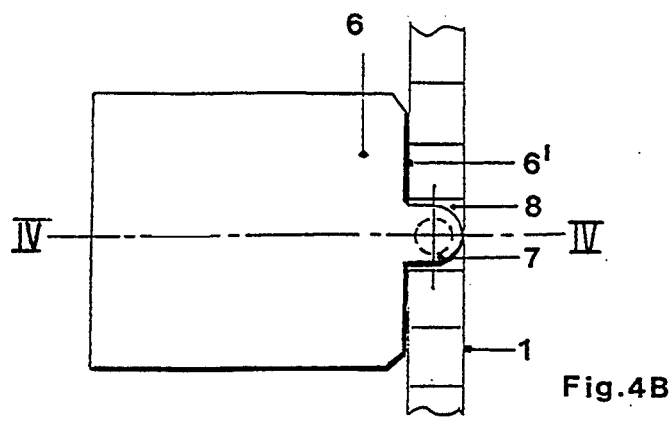
FIG. 4B is a top view of the measuring head shown in FIG. 4A.
Figure 4A:
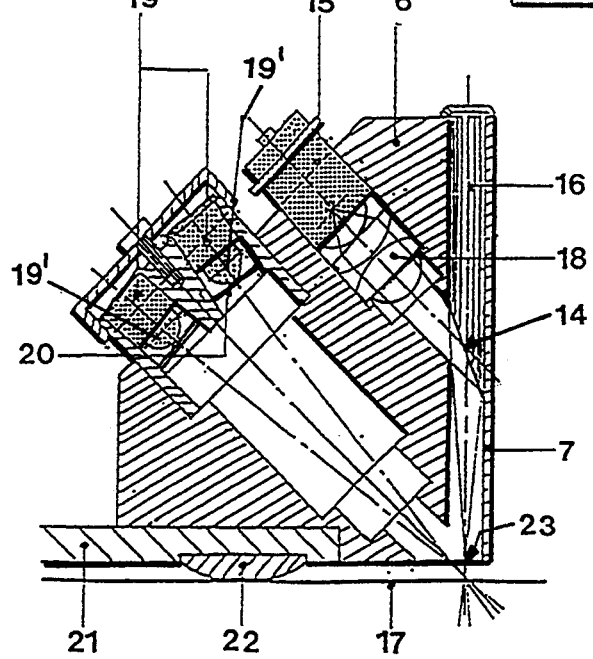
FIG. 4A is a sectional view of the measuring head, along line IV—IV of FIG. 4B.

Hand-held instrument 2 has instrument housing 5 and measuring head 6 in the housing. The measuring head has an outer wall 6' arranged to face a user of the instrument and, as shown in FIG. 4A, it defines measuring aperture 23 facing measuring plane 17. Measuring head 6 contains a source 15 of illuminating light and a light receiver 19. Light guiding channels are arranged in the measuring head to guide the illuminating light from source 15 through measuring aperture 23 to a respective control field 8 in measuring plane 17 and light reflected therefrom through the measuring aperture to light receiver 19. The light guiding channels include a tubular light guiding channel portion 7 rising perpendicularly to measuring plane 17 along outer wall 6' from measuring aperture 23 up measuring head 6. The tubular light guiding channel portion 7 has a uniform cross section throughout the length thereof and this cross section does not exceed that of a control field 8 to be measured. As shown in FIG. 1, the vertically rising light guiding channel portion 7 is an integral part of the measuring head and is contained in a boss slightly protruding from instrument housing 5. As clearly shown in this figure, a user of instrument 2 may readily focus it on a selected control field 8 while looking vertically down and can accurately center it on the selected control field.

As clearly shown in FIG. 4A, tubular light guiding channel portion 7 in measuring head 6 guides illuminating light from source 15 through measuring aperture 23 to control field 8 where it is reflected back through the measuring aperture to light receiver 19. The cross sectional area of tubular light guiding channel portion 7 is adapted to the size of the area of control field 8 so that it is either the same or is preferably a little smaller. As can best be seen in FIG. 4B, if it is a little smaller, it is particularly easy to center the measuring aperture over the selected control field 8 of printing control strip 1 because the margins of the control field remain visible. The tubular light guiding channel portion extends over the entire height of measuring head 6 and has a uniform cross section throughout its length. The cross section is taken transversely to the longitudinal axis of channel portion 7 and, as illustrated in FIG. 4A, is circular.

It is sufficient for an accurate positioning of the measuring head if the user can see the frame of control field 8 under tubular channel portion 7 from the front and from the left and right sides, i.e. from three sides. It is not necessary for the user to be able to see the fourth side, which is blocked from view where the protruding tubular channel portion is connected to the measuring head which contains illuminating light source 15 and light receiver 19, with its photo elements 19' and color filter 20. Generally, control fields 8 have a regular geometric configuration, such as quadratic, rectangular, hexagonal or circular, so that accurate centering of measuring apertures 23 with respect thereto is possible by viewing the control field from three sides.

In addition to the cross sectional area size of tubular light guiding channel portion 7, the shape of this cross section also has an important bearing on the centering of measuring aperture 23 on control field 8. If, as shown in FIG. 1, the side of tubular light guiding channel portion 7 facing a user of the instrument is half-cylindrically shaped, it can be properly centered on a variety of geometrically regularly shaped control fields 8, provided that its cross sectional area does not exceed that of the control field. This cross sectional configuration also makes it possible to position measuring instrument 2 not only parallel to printing control strip 1 but at any desired angle in relation thereto. FIG. 1, for example, shows the instrument held at an acute angle to the printing control strip, which illustrates a preferred ergonomic handling for right-handed users. This cross sectional configuration (most clearly illustrated in FIG. 3) is, therefore, the universally most useful shape.

Figure 2A:
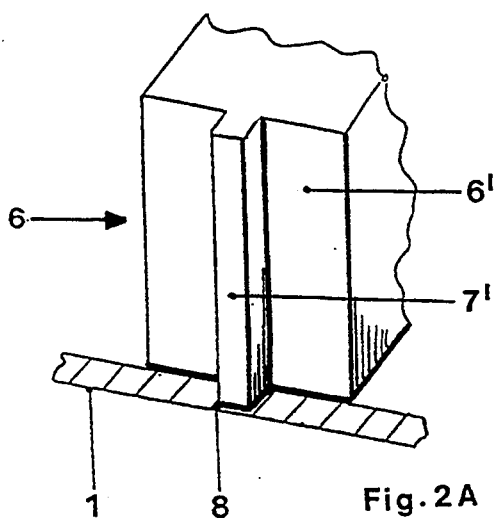
FIGS. 2A, 2B and 2C are fragmentary perspective views illustrating three different embodiments of the tubular light guiding channel portion contained in a measuring head.
Figure 2B:
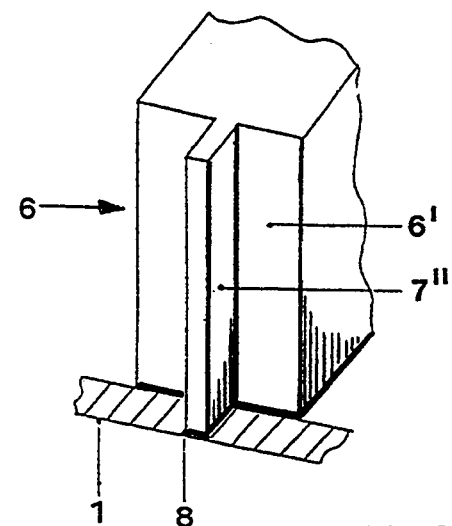
Figure 2C:
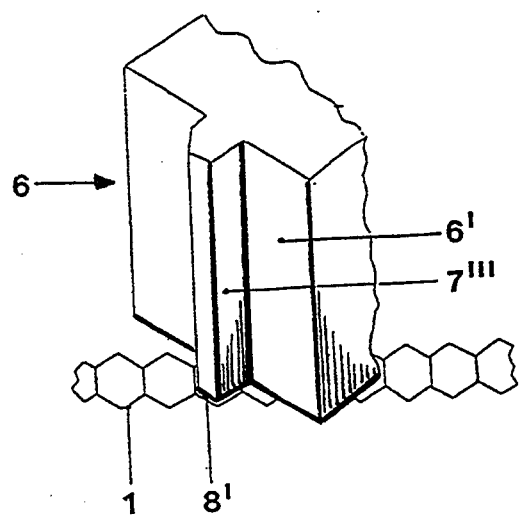

However, the side of the light guiding channel portion facing the user may also have a quadratic cross section (FIG. 2A), a rectangular cross section (FIG. 2B) or a regular polygonal cross section (FIG. 2C), i.e a cross section corresponding to the cross section of the control field. In certain instances, this will facilitate the positioning of measuring aperture 23 in alignment with the center of control field 8. However, this requires instrument 2 to be positioned at a specific angle relative to printing control strip 1. For example, measuring heads 6 with a tubular light guiding channel portion 7' of quadratic cross section can be positioned only parallel or perpendicularly to control strip 1. A measuring head with channel portion 7" of rectangular cross section requires a parallel positioning with respect to the printing control strip. The very narrow rectangular shape shown in FIG. 2B will be particularly useful if very narrow control fields 8 are to be measured. Such control fields sometimes have a width of only 3 mm to enable a large number of control fields 8 to be accommodated in color zones having a width of only 30 to 40 mm. And a channel portion 7'" of regular polygonal cross section can be used in connection with hexagonal control fields at angles of 60° relative to the control strip.

In general, if the cross sectional shape of the tubular light guiding channel portion and the control fields to be measured are the same, accurate centering of the measuring aperture will be facilitated. This is particularly true if the cross sectional area of the channel portion is smaller than that of the control field because the margins of the control field protruding from the tubular channel portion will make it very easy to recognize the correctly centered position.

Figure 3:
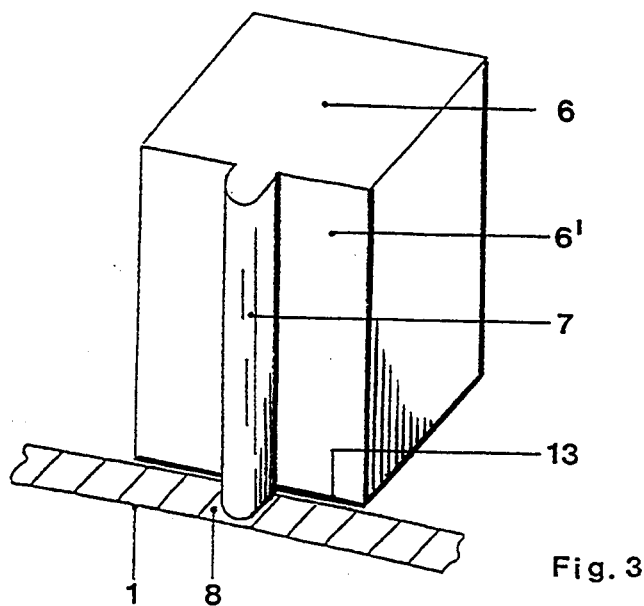
FIG. 3 is a like perspective view illustrating yet another embodiment of the tubular light guiding channel portion.

As shown in FIG. 3, outer wall 6' of measuring head 6, along which tubular light guiding channel portion 7 extends, can also be used for the proper positioning of the measuring head on control field 8. For this purpose, the size and shape of the cross section of channel portion 7 and outer wall 6' are so selected and sized that lower edge 13 of the outer wall runs parallel to printing control strip 1 and is flush therewith or spaced therefrom by no more than a few tenths of a millimeter when measuring aperture 23 is positioned over the center of control field 8. This is the case if the center of an inner, light guiding cross section of tubular light guiding channel portion 7 is spaced a distance from outer wall 6' of measuring head 6 corresponding to, or slightly exceeding, half the width of the control field 8 to be measured, the width extending transversely to a longitudinal extension of printing control strip 1 carrying a succession of said control fields (FIG. 4B). The position of lower edge 13 of outer measuring head wall 6' along the longitudinal edge of printing control strip 1 is particularly easy to observe, and this facilitates a rapid and accurate positioning.

FIG. 4A illustrates some structural details of measuring head 6 in instrument housing 5. The illustrated arrangement of the optic in the measuring head permits a particularly narrow configuration of tubular light guiding channel portion 7 because this portion is arranged in a boss laterally protruding from outer wall 6' of measuring head 6 while the optic, including illuminating light source 15, lens system 18, photosensitive light receiving elements 19, with lenses 19' and color filters 20, are arranged in the measuring head itself. The illustrated measuring head uses a so-called 0°/45° measuring geometry. Accordingly, a glass rod 16 is arranged in tubular light guiding channel portion 7 and the glass rod has an oblique mirrored reflecting face 14 arranged to reflect the illuminating light coming from light source 15 vertically downward through measuring aperture 23 to measuring plane 17.

Lens system 18 is arranged in a portion of the light guiding channels between the illuminating light source and reflecting face 14, which encloses an angle of 45° with channel portion 7, and focusses the illuminating light on measuring plane 17. The light is reflected from the measuring plane through another portion of the light guiding channels enclosing an angle of 45° with measuring plane 17 to photosensitive elements 19 provided with lenses 19', passing through color filters 20. The illustrated densitometer may have four photosensitive elements 19 and a red, green and blue filter 20 for measuring the scale colors cyan blue, magenta and yellow. A fourth photosensitive element for measuring black has no filter or only a brightness correction filter. Color measuring instruments which operate on the three-range principle have only three photosensitive elements for receiving the reflected light, and these elements are provided with conventional tri-stimulus filters.

FIG. 4A shows only two of the three or four photosensitive elements 19 and, for a better understanding, FIG. 4B illustrates only the circumference of measuring head 6 with front wall 6' and tubular light guiding channel portion 7, all seen in top view. It also shows the geometric coordination and positioning of channel portion 7 relative to a control field 8 of printing control strip 1 during a measuring operation, as the measuring aperture is centered on the control field.

Obviously, the arrangement of the optic maybe reversed for a so-called 45°/0° measuring geometry, wherein oblique reflecting face 14 of glass rod 16 is arranged to guide light reflected vertically upward from measuring plane 17 through measuring aperture 23 to photosensitive elements 19 while the illuminating light from source 15 is guided at an angle of 45° to the measuring plane, i.e. the positions of the light source and the light receiver are reversed. This is functionally equivalent to the illustrated arrangement.

As also shown in FIG. 4A, a spacing element 22 is mounted in bottom wall 21 of housing 5 for distancing a lower end of the tubular light guiding channel portion 7 slightly from measuring plane 17. The spacing is just sufficient to avoid placing the vertical tubular light guiding channel portion 7 directly on a possibly freshly printed control strip on which the printing ink may not yet have dried. To assure a parallel positioning of the measuring head on the measuring plane, two or three spacing elements 22 are mounted in the bottom wall of the measuring head.

The conventional elements arranged in housing 5 of known top illumination densitometers for converting the measured interest in the present invention, have not been shown.

What is claimed is:

1. A hand-held instrument for measuring reflections on a colored control field of a printed sheet extending in a measuring plane, which comprises
(a) an instrument housing and
(b) a measuring head in the housing, the measuring head having an outer wall arranged to face a user of the instrument and the measuring head defining a measuring aperture facing the measuring plane, the measuring head containing
    (1) a source of illuminating light,
    (2) a light receiver, and
    (3) light guiding channels arranged to guide the illuminating light from the source through the measuring aperture to a respective one of the control fields in the measuring plane and light reflected therefrom through the measuring aperture to the light receiver, the light guiding channels including a tubular light guiding channel portion rising perpendicularly to the measuring plane along the outer wall from the measuring aperture up the measuring head, and the tubular light guiding channel portion having a uniform cross section throughout the length thereof, the cross section not exceeding that of a control field to be measured.

2. The hand-held measuring instrument of claim 1, wherein the tubular light guiding channel portion has a side facing a user of the instrument, the side of the light guiding channel portion being half-cylindrically shaped.

3. The hand-held measuring instrument of claim 1, wherein the tubular light guiding channel portion has a side facing a user of the instrument, the side of the light guiding channel portion having a quadratic cross section.

4. The hand-held measuring instrument of claim 1, wherein the tubular light guiding channel portion has a side facing a user of the instrument, the side of the light guiding channel portion having a rectangular cross section.

5. The hand-held measuring instrument of claim 1, wherein the tubular light guiding channel portion has a side facing a user of the instrument, the side of the light guiding channel portion having a geometrically regular polygonal cross section.

6. The hand-held measuring instrument of claim 1, wherein the tubular light guiding channel portion has a cross section corresponding to the cross section of the control field.

7. The hand-held measuring instrument of claim 1, wherein the center of an inner, light guiding cross section of the tubular light guiding channel portion is spaced a distance from the outer wall of the measuring head corresponding to half the width of the control field to be measured, the width extending transversely to a longitudinal extension of a printing control strip carrying a succession of said control fields.

8. The hand-held measuring instrument of claim 1, wherein the center of an inner, light guiding cross section of the tubular light guiding channel portion is spaced a distance from the outer wall of the measuring head slightly exceeding half the width of the control field to be measured, the width extending transversely to a longitudinal extension of a printing control strip carrying a succession of said control fields.

9. The hand-held measuring instrument of claim 1, further comprising a glass rod arranged in the tubular light guiding channel portion, the glass rod having an oblique reflecting face arranged to reflect the light from the light source vertically downward through the measuring aperture to the measuring plane.

10. The hand-held measuring instrument of claim 1, further comprising a glass rod arranged in the tubular light guiding channel portion, the glass rod having an oblique reflecting face, and the measuring light receiver comprising photosensitive elements, the oblique reflecting face being arranged to guide light reflected vertically upward from the measuring plane through the measuring aperture to the photosensitive elements.

11. The hand-held measuring instrument of claim 1, further comprising a spacing element for distancing a lower end of the tubular light guiding channel portion slightly from the measuring plane.

* * * * *